US008338652B2

(12) United States Patent
Terada et al.

(10) Patent No.: US 8,338,652 B2
(45) Date of Patent: Dec. 25, 2012

(54) PROCESS FOR PRODUCING 2,3,3,3-TETRAFLUOROPROPENE

(75) Inventors: Junpei Terada, Settsu (JP); Takuji Ishikawa, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 222 days.

(21) Appl. No.: 12/733,612

(22) PCT Filed: Sep. 10, 2008

(86) PCT No.: PCT/JP2008/066804
§ 371 (c)(1),
(2), (4) Date: Mar. 11, 2010

(87) PCT Pub. No.: WO2009/035130
PCT Pub. Date: Mar. 19, 2009

(65) Prior Publication Data
US 2010/0204529 A1    Aug. 12, 2010

(30) Foreign Application Priority Data
Sep. 11, 2007    (JP) .................... 2007-235026

(51) Int. Cl.
C07C 17/00    (2006.01)
C07C 17/10    (2006.01)
(52) U.S. Cl. .................... 570/157; 570/156; 570/176
(58) Field of Classification Search ............ 570/156, 570/157, 176
See application file for complete search history.

(56) References Cited

U.S. PATENT DOCUMENTS

| 2,931,840 A | 4/1960 | Marquis |
| 2,996,555 A | 8/1961 | Rausch |
| 3,996,299 A | 12/1976 | Fozzard |
| 7,906,693 B2 * | 3/2011 | Nappa et al. .................... 570/163 |
| 2006/0217577 A1 | 9/2006 | Mukhopadhyay et al. |
| 2006/0258891 A1 | 11/2006 | Mukhopadhyay et al. |

FOREIGN PATENT DOCUMENTS
JP    63-211245    9/1988
WO    2008/054778    5/2008

OTHER PUBLICATIONS

International Search Report issued Mar. 13, 2009 in International (PCT) Application No. PCT/JP2008/066804.
Written Opinion issued Mar. 13, 2009 in International (PCT) Application No. PCT/JP2008/066804.
R. Eric Banks, et al., "Preparation of 2,3,3,3-tetrafluoropropene from trifluoroacetylacetone and sulphur tetrafluoride", Journal of Fluorine Chemistry, 82, pp. 171-174, 1997.
R.N. Haszeldine et al., "Free-radical Additions to Unsaturated Systems. Part XVII. Reaction of Trifluoroiodomethane with Mixtures of Ethylene and Vinyl Fluoride and of Ethylene and Propene", J. Chem. Soc. (C), 3, pp. 414-421, 1970.
R.N. Haszeldine et al., "Addition of Free Radicals to Unsaturated Systems. Part XIII. Direction of Radical Addition to Chloro-1:1-difluoroethylene", J. Chem. Soc., pp. 2193-2197, 1957.
Vittorio Montanan et al., "A Novel Synthesis of Perhalogenated Alkenes", J. Org. Chem., 57, pp. 5018-5019, 1992.
Tsutomu Konno et al., "Facile syntheses of various per- or polyfluoroalkylated internal acetylene derivatives", Tetrahedron, 59, pp. 7571-7580, 2003.

* cited by examiner

*Primary Examiner* — Jafar Parsa
(74) *Attorney, Agent, or Firm* — Wenderoth, Lind & Ponack, L.L.P.

(57) ABSTRACT

The present invention provides a simple and efficient process for producing 2,3,3,3-tetrafluoropropene(HFC-1234yf), the process being useful for industrial production. More specifically, the present invention relates to:

a process for producing 2,3,3,3-tetrafluoropropene, comprising the steps of:

(I) reacting a compound expressed by Formula (1):

$$CF_3CF_2CH_2X \qquad (1)$$

wherein X represents Cl, Br or I,
with a base to produce a compound expressed by Formula (2):

$$CF_3CF=CHX \qquad (2)$$

wherein X is the same as above; and
(II) reducing the compound expressed by Formula (2) with hydrogen in the presence of a catalyst to produce 2,3,3,3-tetrafluoropropene.

7 Claims, No Drawings

PROCESS FOR PRODUCING 2,3,3,3-TETRAFLUOROPROPENE

TECHNICAL FIELD

The present invention relates to a process for producing 2,3,3,3-tetrafluoropropene($CF_3CF{=}CH_2$).

BACKGROUND ART 2,3,3,3-tetrafluoropropene (hereinafter occasionally referred to as "HFC-1234yf") is attracting attention as a constituent of a mixed refrigerant that serves as a substitute for CFC.

As one example of a process for producing HFC-1234yf, Non-Patent Document 1 discloses a method comprising only one step: reacting $CF_3CF_2CH_2X$ (X=Cl or I) with zinc (Zn) in ethanol. However, this process is not suitable for industrial production because of the high cost of zinc and production of wastes.

Patent Documents 1 to 5 and Non-Patent Documents 2 and 3 disclose alternative methods of HFC-1234yf production. However, they also have some drawbacks, such as a difficulty in the production of starting material, severe reaction conditions, high costs for the reaction reagent, or a low yield. These production methods are thus not sufficiently effective for industrial production.

Patent Document 1: Japanese Unexamined Patent Publication No. 1988-211245
Patent Document 2: Specification of U.S. Pat. No. 3,996,299
Patent Document 3: Specification of US Patent Publication No. 2006/258891
Patent Document 4: Specification of U.S. Pat. No. 2,996,555
Patent Document 5: Specification of U.S. Pat. No. 2,931,840
Non-patent document 1: J. Chem. Soc., 1957, 2193-2197
Non-patent document 2: J. Chem. Soc., 1970, 3, 414-421
Non-patent document 3: J. Flu. Chem., 1997, 82, 171-174

DISCLOSURE OF THE INVENTION

The present invention was made in view of the foregoing problem in the existing art, and a major object is to provide a simple and efficient process for producing 2,3,3,3-tetrafluoropropene (HFC-1234yf) that is useful for industrial production.

The inventors of the present invention conducted an extensive study to attain the foregoing object, and found a simple and efficient process for producing HFC-1234yf comprising reacting inexpensive and readily available 1-chloro-2,2,3,3,3-pentafluoropropane ($CF_3CF_2CH_2Cl$) with a base such as potassium hydroxide, thereby producing 1-chloro-2,3,3,3-pentafluoropropene ($CF_3CF{=}CHCl$); and reducing the resulting 1-chloro-2,3,3,3-pentafluoropropene ($CF_3CF{=}CHCl$) with hydrogen in the presence of a catalyst. After conducting additional research based on this finding, the inventors completed the present invention.

Specifically, the present invention provides the following processes for producing HFC-1234yf.

Item 1: A process for producing 2,3,3,3-tetrafluoropropene, comprising the steps of:
(I) reacting a compound expressed by Formula (1):

wherein X represents Cl, Br or I,
with a base to produce a compound expressed by Formula (2):

wherein X is the same as above; and
(II) reducing the compound expressed by Formula (2) with hydrogen in the presence of a catalyst to produce 2,3,3,3-tetrafluoropropene.

Item 2: A process according to item 1, wherein the step (I) is performed in a medium containing water.

Item 3: A process according to item 1, wherein the step (I) is performed in a medium containing water and a hydrophobic organic solvent.

Item 4: A process according to item 3, wherein a surfactant is used in the step (I).

Item 5: A process according to item 3, wherein a phase-transfer catalyst is used in the step (I).

Item 6: A process according to any one of items 1 to 5, wherein, in the step (I), X in the Formulas (1) and (2) represents Cl.

Item 7: A process according to any one of items 1 to 6, wherein the base used in the step (I) is alkali metal hydroxide.

Item 8: A process according to any one of items 1 to 7, wherein palladium-carbon (Pd—C) is used as a catalyst in the step (II).

Item 9: A process according to any one of items 1 to 8, wherein the step (II) is performed in a medium containing water in the presence of a base.

Item 10: A process for producing a compound expressed by Formula (2):

$$CF_3CF{=}CHX \qquad (2)$$

wherein X represents Cl, Br or I,
the process comprising the step of reacting a compound expressed by Formula (1):

$$CF_3CF_2CH_2X \qquad (1)$$

wherein X is the same as above,
with a base.

EFFECT OF THE INVENTION

The process according to the present invention not only ensures simple and efficient production of 2,3,3,3-tetrafluoropropene (HFC-1234yf) but also has some advantages in HFC-1234yf production, including the use of an inexpensive reagent, moderate reaction conditions, and a high yield. These advantages make the process of the present invention suitable for industrial production.

BEST MODE FOR CARRYING OUT THE INVENTION

The present invention is a process for producing 2,3,3,3-tetrafluoropropene, comprising the steps of:
(I) reacting a compound expressed by Formula (1):

wherein X expresses Cl, Br or I,
with a base to produce a compound expressed by Formula (2):

wherein X is the same as above; and
(II) reducing the compound expressed by Formula (2) with hydrogen in the presence of a catalyst to produce 2,3,3,3-tetrafluoropropene.

X can be any of Cl, Br or I, but preferably Cl. The compound expressed by Formula (1) is commercially available or can be produced easily by any known method, for example, in accordance with the teaching of Japanese Unexamined Patent Publication No. 1990-204428, Japanese Unexamined Patent Publication No. 1991-127747, or U.S. Pat. No. 3,038,947.

Step (I):

Step (I) carries out HF-elimination by reacting the compound expressed by Formula (1) with a base, thereby producing the compound expressed by Formula (2).

The reaction can be performed in a medium, and a medium that contains water is generally used. The water-containing medium may also contain other media (e.g., organic solvent); for example, an aromatic hydrocarbon such as benzene, toluene, or (o-, m-, or p-) xylene; an aliphatic hydrocarbon such as hexane, octane, or nonane; or an ether such as diethylether or tetrahydrofuran. Among these, a hydrophobic organic solvent such as an aromatic hydrocarbon or an aliphatic hydrocarbon is preferred, and more specifically, a solvent whose boiling point is not less than 100° C., such as toluene or xylene, is preferred.

The entire amount of the medium is generally 1 to 15 parts by weight, preferably 2 to 10 parts by weight, per part by weight of the compound expressed by Formula (1). In the medium, the weight ratio of water to the other medium is generally 100:0 to 10:90, and preferably 70:30 to 30:70.

The base serves to facilitate the HF-elimination reaction and to form a carbon-carbon double bond. Either an organic base or an inorganic base can be used, as long as it is water soluble. Examples of organic bases include trialkylamines such as triethylamine or diisopropylethylamine. Examples of inorganic bases include alkali metal hydroxides such as potassium hydroxide or sodium hydroxide; alkaline earth metal hydroxides such as calcium hydroxide; and metal oxides such as magnesium oxide. Among these, an alkali metal hydroxide is preferable, and potassium hydroxide is more preferable.

The amount of the base is generally 1 to 5 mol, preferably 1.5 to 3.5 mol, per mol of the compound expressed by Formula (1). The yield tends to increase as the amount of the base increases.

The foregoing reaction medium generally contains water and a organic solvent (a hydrophobic organic solvent, in particular). When the reaction medium forms two phases, the reaction medium may also contain a surfactant, a phase-transfer catalyst, etc. in order to facilitate the reaction between the substances in the respective phases.

Examples of surfactants include nonionic surfactants such as aliphatic diethanol amide; cationic surfactants such as alkyltriethyl ammonium salt; anionic surfactants such as monoalkyl sulfate; and amphoteric surfactants such as alkylcarboxybetaine. An amphoteric surfactant is particularly preferable because of its heat resistance.

When the medium contains a surfactant, the amount of the surfactant is generally 0.0005 to 0.10 parts by weight, preferably 0.0008 to 0.05 parts by weight, per part by weight of water used as a medium. Specific examples of surfactants include Anon BF (produced by Nippon Oil & Fats Co., Ltd.) and Anon BL (produced by Nippon Oil & Fats Co., Ltd.).

Examples of phase-transfer catalysts include quaternary ammonium salts such as tetrabutyl ammonium bromide (TBAB), trimethyl benzyl ammonium bromide, triethyl benzyl ammonium bromide, or trioctyl methyl ammonium chloride (TOMAC); phosphonium salts such as tetrabutyl phosphonium chloride (TBPC); and crown ethers such as 15-crown 5, or 18-crown 6.

When the medium contains a phase-transfer catalyst, the amount of the phase-transfer catalyst is generally 0.1 to 10 mol %, preferably 0.5 to 5 mol %, based on the compound expressed by Formula (1).

In the reaction, the reaction temperature is generally 10 to 150° C., and preferably 30 to 130° C. The reaction pressure is generally −0.1 to 10 MPa·G, and preferably 0 to 5 MPa·G.

When using a phase-transfer catalyst, the reaction can be performed under particularly moderate conditions; in this case, the reaction temperature ranges from 10 to 80° C., and preferably 20 to 50° C.; and the reaction pressure ranges from −0.1 to 10 MPa·G, and preferably 0 to 5 MPa·G. The use of a phase-transfer catalyst also greatly increases the conversion, selectivity and yield. The reaction is generally performed while stirring under the foregoing conditions. The reaction time depends on the reaction conditions, but is generally about 1 to 9 hours.

The progress of the reaction can be monitored by taking a gas sample from the reaction system and analyzing the components of the gas phase portion using gas chromatography. The obtained product containing the compound expressed by Formula (2) generally has a low boiling point (e.g., the boiling point is about 15° C. where X=Cl); therefore, the resultant product of the reaction can be cooled with a cryogen before being collected by fractional distillation or a like method.

With such a process, the production of the compound expressed by Formula (2) can be carried out while ensuring a high conversion, high selectivity, and a high isolated yield under moderate conditions.

Step (II):

Using the compound expressed by Formula (2) thus obtained in Step (I), Step (II) reduces the compound with hydrogen in the presence of a catalyst, thereby producing the target 2,3,3,3-tetrafluoropropene.

This reaction can be carried out in a medium, which generally contains water. The entire amount of the medium is generally 1 to 10 parts by weight, and preferably 3 to 7 parts by weight, per part by weight of the compound expressed by Formula (2). The amount of hydrogen is generally 1 to 1.2 mol, and preferably 1.05 to 1.1 mol, per mol of the compound expressed by Formula (2).

The catalyst used for the catalytic hydrogenation is preferably a palladium-carrying catalyst. A typical example is a catalyst in which palladium is supported by activated carbon, i.e. palladium-carbon (Pd—C). The amount of the palladium-carrying catalyst is 0.001 to 0.01 parts by weight, and preferably 0.002 to 0.004 parts by weight, per part by weight of the compound expressed by Formula (2).

Further, in the reaction, the catalyst is preferably poisoned. For example, potassium sulfate ($K_2SO_4$), barium sulfate ($BaSO_4$), sodium sulfate ($Na_2SO_4$) or the like may be added to the reaction system as a poisoning substance.

Among these poisoning agents, potassium sulfate is the most preferable in terms of its price, solubility, etc. The amount of the poisoning agent is generally 0.1 to 5 mol, and preferably 1 to 3 mol, per mol of the palladium-carrying catalyst.

The reaction is usually carried out batch-wise. The temperature in the reaction process is generally 0 to 50° C., and preferably 0 to 20° C. The reaction pressure is generally 0.05 to 1.0 MPa·G, and preferably 0.1 to 0.5 MPa·G. The reaction is generally performed while stirring under the foregoing conditions. The reaction time depends on the reaction conditions, but is generally about 8 to 12 hours.

The progress of the reaction can be monitored by taking a gas sample from the reaction system and analyzing the components of the gas phase portion using gas chromatography. The obtained product containing the compound expressed by Formula (2) generally has a low boiling point (−28.3° C.); therefore, the resultant product of the reaction is cooled with a cryogen before being collected by fractional distillation or the like.

Using such a process, 2,3,3,3-tetrafluoropropene can be produced from the compound expressed by Formula (2) while ensuring a high conversion, high selectivity, and a high isolated yield.

The 2,3,3,3-tetrafluoropropene obtained through the method of the present invention can be applied to various fields. Since the global warming potential and ozone depletion potential of this compound are both small, the compound is useful as, for example, a constituent of a mixed refrigerant (e.g., a refrigerant for a car air conditioner or the like), for use as a CFC substitute.

EXAMPLES

The following describes Examples of the present invention to further clarify the features of the present invention. However, the present invention is not limited to these Examples.

Example 1

90.2 g of water, 16.8 g of KOH, and 0.150 g of Anon BF (produced by Nippon Oil & Fats Co. Ltd.) as a surfactant were placed in a 200-ml SUS autoclave equipped with a manometer, a thermometer, a gas removal valve and a safety valve, and fully suspended using a mechanical stirrer. Under ice-cooling, the device was purged with nitrogen, followed by pressure reduction using a vacuum pump, before being supplied with 27.7 g (0.150 mol) of $CF_3CF_2CH_2Cl$ (purity=91.3%). As a result, the temperature increased from 6° C. to 7.5° C.

After the process was completed, the reaction mixture was stirred at 1000 rpm, and heated to 120° C. using a band heater. The measured pressure at this stage was 0.5 MPa·G. A gas sample was taken every hour at 120° C., and the composition of the gas phase was analyzed using gas chromatography. After a 4-hour reaction, the reactant was further heated to 130° C. before another reaction of 5 hours. The measured pressure at this stage was 0.7 MPa·G.

After the reaction for a total of 9 hours, the reactor was set to 80° C., and the gas component was removed from the reactor and collected. Since the boiling point of the main product ($CF_3CF=CHCl$) was 15.0° C., the product was collected using a cryogen made of dry ice and acetone. The collected product was analyzed using gas chromatography. The conversion was 92.3%, the selectivity was 51.0%, and the isolated yield was 47.1%.

Example 2

45.4 g of water, 8.5 g of KOH, 0.145 g of Anon BF (produced by Nippon Oil & Fats Co. Ltd.) as a surfactant, and 53.7 g of o-xylene were placed in the same device as that of Example 1, and fully suspended using a mechanical stirrer. Under ice-cooling, the device was purged with nitrogen, followed by pressure reduction using a vacuum pump, before being supplied with 12.7 g (0.0751 mol) of $CF_3CF_2CH_2Cl$ (purity=93.7%). As a result, the temperature increased from 6.4° C. to 8.5° C.

After the process was completed, the reaction mixture was stirred at 1,000 rpm, and heated to 100° C. using a band heater. The measured pressure at this stage was 0.14 MPa·G. A gas sample was taken every hour at 100° C., and the composition of the gas phase was analyzed using gas chromatography. The reaction was carried out for 3.5 hours at a pressure of 0.17 MPa·G.

After the reaction for a total of 3.5 hours, the reactor was set to 80° C., and the gas component was removed from the reactor and collected. Since the boiling point of the main product ($CF_3CF=CHCl$) was 15.0° C., the product was collected using a cryogen made of dry ice and acetone. The collected product was analyzed using gas chromatography. The conversion was 67.5%, the selectivity was 94.3%, and the isolated yield was 67.3%.

Example 3

11.8 g of water, 9.6 g of KOH, 0.430 g of Anon BF (produced by Nippon Oil & Fats Co. Ltd.) as a surfactant, and 20.9 g of o-xylene were placed in the same device as that of Example 1, and fully suspended using a mechanical stirrer. Under ice-cooling, the device was purged with nitrogen, followed by pressure reduction using a vacuum pump, before being supplied with 6.87 g (0.0395 mol) of $CF_3CF_2CH_2Cl$ (purity=96.9%). As a result, the temperature increased from 4.9° C. to 7.4° C.

After the process was completed, the reaction mixture was stirred at 1,000 rpm, and heated to 100° C. using a band heater. The measured pressure at this stage was 0.11 MPa·G. A gas sample was taken every hour at 100° C., and the composition of the gas phase was analyzed using gas chromatography. The reaction was carried out for 4 hours at a pressure of 0.18 MPa·G.

After the 4-hour reaction in total, the reactor was set to 80° C., and the gas component was removed from the reactor and collected. Since the boiling point of the main product ($CF_3CF=CHCl$) was 15.0° C., the product was collected using a cryogen made of dry ice and acetone. The collected product was analyzed using gas chromatography. The conversion was 97.8%, the selectivity was 87.2%, and the isolated yield was 84.9%.

Example 4

50.5 g of water, 37.8 g of KOH, 2.18 g of tetrabutyl ammonium bromide(TBAB) as a phase-transfer catalyst, and 52.0 g of o-xylene were placed in the same device as that of Example 1, and fully suspended using a mechanical stirrer. Under ice-cooling, the device was purged with nitrogen, followed by pressure reduction using a vacuum pump, before being supplied with 40.0 g (0.227 mol) of $CF_3CF_2CH_2Cl$ (purity=95.8%). As a result, the temperature increased from 7.0° C. to 11.5° C.

After the process was completed, the reaction mixture was stirred at 1,000 rpm, and heated to 50° C. using a band heater. The measured pressure at this stage was 0.08 MPa·G. A gas sample was taken every hour at 50° C., and the composition of the gas phase was analyzed using gas chromatography. The reaction was carried out for 2 hours at a pressure of 0.09 MPa·G.

After the 2-hour reaction in total, the reactor was set to 80° C., and the gas component was removed from the reactor and collected. Since the boiling point of the main product ($CF_3CF=CHCl$) was 15.0° C., the product was collected using a cryogen made of dry ice and acetone. The collected product was analyzed using gas chromatography. The conversion was 100%, the selectivity was 76.0%, and the isolated yield was 76.0%.

Example 5

0.0545 g of Pd—C catalyst (type-K: produced by NE-Chemcat, 5 wt % Pd, moisture content=50% (C)), 0.00826 g of $K_2SO_4$, 4.2 g of KOH, and 65.8 g of water were placed in a 200-ml SUS autoclave equipped with a manometer, a thermometer, a gas removal valve and a safety valve, and fully suspended using a mechanical stirrer.

While being cooled with ice, the device was purged with nitrogen, followed by pressure reduction using a vacuum pump, before being supplied with 10.7 g (0.0670 mol) of $CF_3CF=CHCl$ (purity=93.3%). Also, the device was connected to a 300-ml cylinder filled with 1.30 MPa·G of hydrogen. After the process was completed, the reaction mixture was stirred at 1,000 rpm, and kept at 1 to 2° C. with ice and water. The measured pressure at this stage was −0.02 MPa·G. In this state, hydrogen was supplied to the device from an attached hydrogen cylinder until the internal pressure became 0.3 MPa·G. The amount of hydrogen supplied was 0.0283 mol.

After an hour, the internal pressure decreased to around 0.1 MPa·G and hydrogen was again supplied in the same manner. This process was repeated for 4.5 hours until 0.0737 mol in total of hydrogen was supplied. A gas sample was taken every hour, and the composition of the gas phase was analyzed using gas chromatography. The reaction was carried out for a total of 10.4 hours at a pressure of 0.16 MPa·G.

After the reaction was completed, the reactor was kept at 1 to 2° C., and the gas component was removed from the reactor and collected. Since the boiling point of the main product ($CF_3CF=CH_2$) was −28.3° C., the product was collected using a cryogen made of dry ice and acetone. The collected product was analyzed using gas chromatography. The conversion was 95.3%; the selectivity was 90.1%; and the isolated yield was 85.9%. The by-product was $CF_3CHFCH_3$.

The invention claimed is:

1. A process for producing 2,3,3,3-tetrafluoropropene, comprising the steps of:

(I) reacting a compound expressed by Formula (1):

$$CF_3CF_2CH_2X \qquad (1)$$

wherein X represents Cl, Br or I,
   with a base to produce a compound expressed by Formula (2):

$$CF_3CF=CHX \qquad (2)$$

wherein X is the same as above;
   and (II) reducing the compound expressed by Formula (2) with hydrogen in the presence of a catalyst to produce 2,3,3,3-tetrafluoropropene,
   wherein step (I) is performed in a medium containing water and a hydrophobic organic solvent, and
   wherein a surfactant and/or a phase-transfer catalyst is/are used in step (I).

2. A process according to claim 1, wherein the surfactant is used in the step (I).

3. A process according to claim 1, wherein the phase-transfer catalyst is used in the step (I).

4. A process according to claim 1, wherein, in the step (I), X in the Formulas (1) and (2) represents Cl.

5. A process according to claim 1, wherein the base used in the step (I) is alkali metal hydroxide.

6. A process according to claim 1, wherein palladium-carbon (Pd—C) is used as a catalyst in the step (II).

7. A process according to claim 1, wherein the step (II) is performed in a medium containing water in the presence of a base.

* * * * *